United States Patent [19]
Schmutz

[11] Patent Number: 6,054,471
[45] Date of Patent: Apr. 25, 2000

[54] USE OF FLUORINATED TRIAZOLES IN TREATING NEUROPATHIC PAIN

[75] Inventor: Markus Schmutz, Schoenenbuch, Switzerland

[73] Assignee: Novartis AG, Basel, Switzerland

[21] Appl. No.: 09/259,911

[22] Filed: Mar. 1, 1999

[51] Int. Cl.[7] .................................................... A61K 31/41
[52] U.S. Cl. ............................................................ 514/359
[58] Field of Search ................................................ 514/359

[56] References Cited

U.S. PATENT DOCUMENTS 4,789,680  12/1988  Meier ........................................ 514/359

*Primary Examiner*—William R. A. Jarvis
*Attorney, Agent, or Firm*—Joseph J. Borovian

[57] ABSTRACT

The present invention relates to the use of fluorinated triazoles in treating neuropathic pain.

2 Claims, No Drawings

USE OF FLUORINATED TRIAZOLES IN TREATING NEUROPATHIC PAIN

The present invention relates to a new pharmaceutical use of fluorinated triazoles.

More particularly the present invention relates to a new pharmaceutical use for compounds of formula I

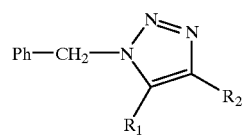

wherein Ph is an o-fluorinated phenyl radical which may be additionally substituted by 1 or 2 halogen atoms selected from fluorine and chlorine, $R_1$ is hydrogen, carbamoyl, N-$(C_2-C_5)$alkanoylcarbamoyl or N,N-di$(C_1-C_4)$alkylcarbamoyl, and $R_2$ is carbamoyl, N-$(C_2-C_5)$alkanoylcarbamoyl or N,N-di$(C_1-C_4)$alkylcarbamoyl.

The compounds of formula I as well as their production process are known e.g. from European Patent No. 199 262. This patent also discloses the use of the compounds of formula I for the treatment of convulsions of different origin, e.g. of epilepsy.

In accordance with the present invention, it has now surprisingly been found that the compounds of formula I are useful in the treatment of neuropathic pain.

The activity of the compounds of formula I in said treatment is evidenced, for example, in the following models of neuropathic pain in the rat and guinea-pig:

Wistar rats or Dunkin Hartley guinea pigs are anesthetized with enflurane (in $N_2O:O_2$ for guinea pigs) and the left sciatic nerve is exposed and partially ligated with thread. This procedure produces a mechanical hyperalgesia which develops within 2–3 days and is maintained for at least 4 weeks. Paw withdrawal thresholds to a pressure stimulus are measured using an analgesymeter. Mechanical thresholds are taken on both the ipsilateral (ligated) and contralateral (unligated) paw prior to and then up to 6 hours following drug or vehicle administration. Reversal of hpyeralgesia at each time point is calculated. Groups of 6 animals are used. Statistical analysis is carried out on withdrawal threshold readings using ANOVA followed by Tukey's HSD test.

In the rat model, the compounds of formula I significantly reverse neuropathic mechanical hyperalgesia at doses of about 10 to about 300 mg/kg p.o. With the compound 1-(2,6-difluorophenyl)methyl-1H-1,2,3-triazole-4-carboxamide, for example, a maximal reversal of neuropathic mechanical hypderalgesia of 30% is achieved after 3 hours on adminstration of 10 mg/kg p.o.

In the guinea pig model, the compounds of formula I significantly reverse neuropathic mechanical hyperalgesia at doses of about 3 to about 100 mg/kg p.o. With the above-mentioned carboxamide, for example, a maximal reversal of neuropathic mechanical hyperalgesia of 60% is achieved after 3 hours on administration of 30 mg/kg p.o.

The compounds of formula I are therefore useful in the treatment of neuropathic pain and associated hyperalgesia, including trigeminal and herpetic neuralgia, diabetic neuropathic pain, migraine, causalgia and deafferentation syndromes such as brachial plexus avulsion.

In a preferred group of formula I for use according to the invention, Ph is o-fluorophenyl, 2,5-difluorophenyl, 2,6-difluorophenyl or 2-chloro-6-fluorophenyl, $R_1$ is hydrogen or carbamoyl and $R_2$ is carbamoyl. The above-mentioned carboxamide is particularly preferred.

For the above-mentioned indications the appropriate dosage will of course vary depending upon, for example, the compound employed, the host, the mode of administration and the nature and severity of the condition being treated. However, in general, satisfactory results in animals are indicated to be obtained at a daily dosage of from about 1 to about 50 mg/kg animal body weight. In larger mammals, for example humans, an indicated daily dosage is in the range from about 50 to about 3500 mg of a compound according to the invention conveniently administered, for example, in divided doses up to four times a day.

The compounds of formula I may be administered in any usual manner, e.g. orally, for example in the form of tablets or capsules, or parenterally, for example in the form of injection solutions or suspensions.

The present invention also provides pharmaceutical compositions comprising a compound of formula I in association with at least one pharmaceutical carrier or diluent, for use in the treatment of neuropathic pain. Such compositions may be manufactured in conventional manner. Unit dosage forms may contain for example from about 10 mg to about 1500 mg of the compound of formula 1.

For example tablets each containing 50 mg, or film-coated tablets each containing 100 mg, of 1-(2,6-difluorophenyl) methyl-1H-1,2,3-triazole-4-carboxamide, may be prepared as described in Examples 15 and 16 of EP 199262.

The invention further provides the use of a compound of formula I for the manufacture of a pharmaceutical composition for the treatment of neuropathic pain.

The invention furthermore provides a method for the treatment of neuropathic pain in a subject in need of such treatment, which comprises administering to said subject a therapeutically effective amount of a compound of formula 1.

What is claimed is:

1. A method for the treatment of neuropathic pain and associated hyperalgesia in a subject in need of such treatment, which comprises administering to said subject a therapeutically effective amount of a compound of formula I

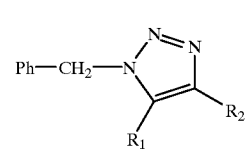

wherein Ph is an o-fluorinated phenyl radical which may be additionally substituted by 1 or 2 halogen atoms selected from fluorine and chlorine, $R_1$ is hydrogen, carbamoyl, N-$(C_2-C_5)$alkanoylcarbamoyl or N, N-di$(C_1-C_4)$alkylcarbamoyl, and $R_2$ is carbamoyl, N-$(C_2-C_5)$alkanoylcarbamoyl or N,N-di$(C_1-C_4)$alkylcarbamoyl.

2. The method according to claim 1, wherein the compound of formula I administered is 1-(2,6-difluorophenyl) methyl-1H-1,2,3-triazole-4-carboxamide.

* * * * *